United States Patent [19]
Takeuchi

[11] Patent Number: 6,116,899
[45] Date of Patent: *Sep. 12, 2000

[54] DENTAL PROBE FOR MEASURING AND EXPLORING THE DEPTH OF A BLIND POCKET FORMED AROUND A TOOTH

[76] Inventor: Hideyuki Takeuchi, T612 9-41, Kyomachi, Fusimi-Ku, Kyouyo City, Kyoto-Pref., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/869,523

[22] Filed: Jun. 6, 1997

[30] Foreign Application Priority Data

Jul. 25, 1996 [JP] Japan ................................ 8-008180

[51] Int. Cl.$^7$ ................................ A61C 19/04
[52] U.S. Cl. ................................ 433/72; 433/29; 433/75
[58] Field of Search ................................ 433/72, 29, 75; 33/513, 514; 600/589, 590

[56] References Cited

U.S. PATENT DOCUMENTS

| | | | |
|---|---|---|---|
| 4,501,555 | 2/1985 | Ditchburn | 433/72 |
| 5,178,537 | 1/1993 | Currie | 433/72 |
| 5,271,734 | 12/1993 | Takeuchi | 433/72 |
| 5,423,677 | 6/1995 | Brattesani | 433/72 |

*Primary Examiner*—John J. Wilson
*Attorney, Agent, or Firm*—Chadbourne & Parke LLP

[57] ABSTRACT

An one-piece dental probe made of light condensing fluorescent plastic comprising a handle, a distal portion and a measuring needle for measuring and exploring blind gum pockets is provided. The measuring needle has at least one visible measurement gradation for measuring the depth of the blind pocket. Light collected at the distal end of the probe is reflected through the probe and illuminates the vicinity of the blind pocket, thus enabling accurate measurement of the depth of the blind pocket in low-light conditions. The tip of the measuring needle may be hemispherical, and form an annular ledge around the needle for probing the existence and location of tartar and other foreign matters in the blind pocket.

5 Claims, 5 Drawing Sheets

DENTAL PROBE FOR MEASURING AND EXPLORING THE DEPTH OF A BLIND POCKET FORMED AROUND A TOOTH

FIELD OF THE INVENTION

This invention relates to a dental probe used to monitor the progress of periodontal disease and more particularly, to a dental probe that is used to measure the depth of a blind pocket formed around a tooth in low light conditions and to probe tartar and foreign matters on the root of a tooth lodged in the blind pocket.

BACKGROUND OF THE INVENTION

When a person is afflicted with periodontal disease and gum inflammation progresses, tissue around teeth is destroyed and blind pockets are formed. In order to effectively treat the disease, it is necessary to measure the depth of the blind pocket to determine the course of the gingivitis.

One commonly used measuring probe is a metal rod having a head and a thin doglegged metal measuring needle attached thereto. Gradations are etched on the measuring needle of the head. When the tip of this measuring needle is inserted into the blind pocket, the pocket's depth can be measured by observing which gradations remain visible.

But the thin metal needle tip can easily wound the patient's gum when inserted into the affected area, and the device may not give accurate measurements because the needle tip cannot be accurately positioned at the bottom of the blind pocket.

Furthermore, this device does not give accurate measurements because the patient's mouth cavity is dark. In the case of group dental examinations that frequently take place in schools and companies, the lighting is often inadequate for examination purposes and it is difficult for the user to see the fine gradation cuts on the thin needle.

The tool must also be well sterilized after each use in order to avoid infection of contagious disease such as AIDS and B-type hepatitis. This takes time and is impractical where hundreds of persons are being examined in a group dental examination at a school or a company. In such a situations, tools are often re-used after being quickly sterilized, but such a simplified sterilization is not sufficient, and inflammation of a mouth region is often transmitted to other patients.

U.S. Pat. No. 5,271,734, issued in 1993, attempted to address these deficiencies in the art. In that invention, the handle includes a light source and is w coupled to the measuring probe attachment in a secure yet easily removable way. The device is sanitary because the measuring probe can be replaced with a new one after being contaminated by a diseased mouth region. The measuring portion is made of optical plastic and has preselected spacing indicators to emit light provided by a light source. The light source consists of a battery and a miniature bulb in the handle.

But the device is expensive to manufacture because it consists of two separate pieces, and it is cumbersome and difficult to maneuver in the mouth cavity because of the light source being built into the handle.

Another dental probe is described in registered Japanese utility model No. 1704625. It is an object of that invention to suppress secondary microbe infections by using polyacetar plastic for the probe, to which microbes do not adhere. Dentists can measure the depth of a blind pocket by inserting the cut or colored needle to the area between the gum and the tooth. Unlike the traditional stainless probe, it is possible to insert the polyacetate measuring probe into a space between teeth without damaging the gum. However, it is difficult for the user to see the fine gradation cuts on the thin needle because the patient's mouth cavity is dark. To improve the visibility, the cuts can be given various colors, but the production cost becomes high. Even if the cuts are colored, it is difficult to see cuts under the bad conditions of poor lighting facilities in schools or companies.

Aside from the deficiencies, there are no devices that can be used to probe and locate the tartar and other foreign matters in blind pockets. If the tartar is not removed in the early stages, it can cause Riggs' disease. Presently, dentists and their assistants must rely on intuition and guesswork to remove the tartar from the blind pocket with a scaler.

It is therefore an object of this invention to provide a dental probe for measuring the depth of a blind pocket that can be accurately employed in low-light conditions, and that is easily manufactured, relatively inexpensive and lightweight.

It is a further object of this invention to provide a dental probe that does not injure the gum tissue and that does not require sterilization after each use.

It is yet a further object of this invention to provide a dental probe that can also be used to probe the location of tartar and other foreign matters in a blind gum pocket.

SUMMARY OF THE INVENTION

A dental probe made of transparent plastic containing fluorescent dye and having a distal end and a needle end is provided. The user can easily see the fine gradation cuts on the thin needle even in a dark mouth cavity because the light collected at the distal end is conducted through the handle of the probe and is emitted at the needle end. The probe can be used in low-light conditions because the handle end of the probe traps much of the available light, which is then reflected to the needle end in the mouth cavity, making the gradations on the measuring needle easily visible.

The probe is one piece and is easily manufactured using injection molding. The probe is thus inexpensive and disposable, so a new probe can be used for each patient. This eliminates the risk of transmission of infection from patient to patient. Also, because it is plastic and may have a hemispherical needle tip, the probe will not damage the gum tissue. The hemispherical tip is also preferably larger in diameter than the needle itself, so an annular ledge is formed at the junction of the tip and the needle, which can be used to probe the location of tartar and other foreign matters in blind gum pockets.

DETAILED DESCRIPTION

Figure 1:
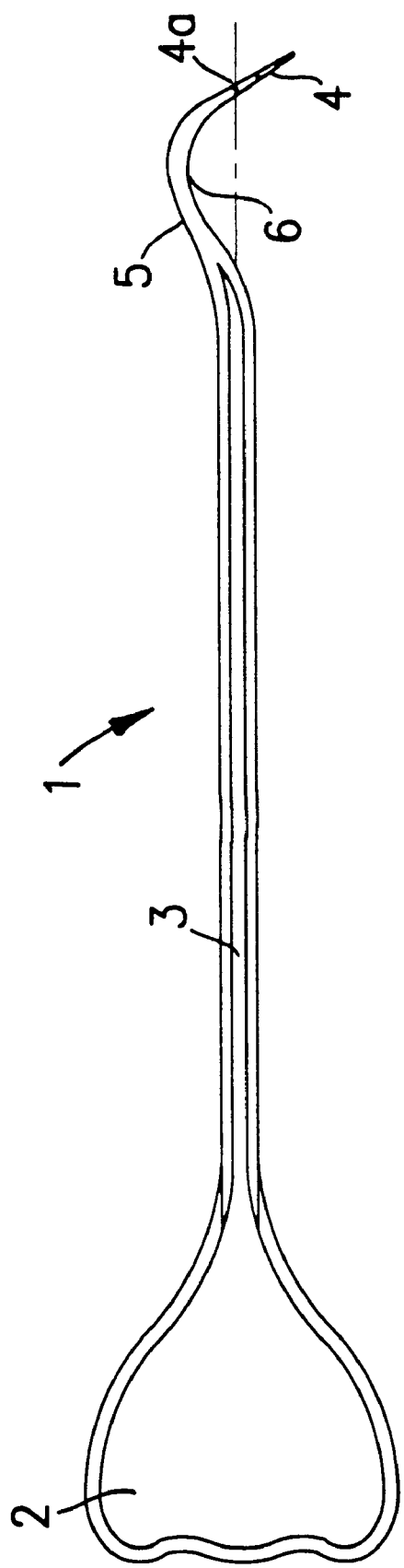
FIG. 1 shows an embodiment of the dental probe for measuring gum pockets.

As shown in FIG. 1, the dental probe 1 for measuring gum pockets is a unitary piece and consists of a distal end 2, a handle 3 and a measuring needle 4. The measuring needle 4 may also have a first curve 5 and a second curve 6 with an angle of approximately 60° against the rod handle 3.

The distal end 2 of the probe 1 collects exterior light and transmits it through the handle 3 to at least one aperture in the edge portion 4a of the measuring needle 4 by reflecting the light through the reflective plastic. The strength of the light emitted from at the edge 4a of the needle 4 is directly proportional to the area of the distal end 2. The area of the distal end 2 is therefore preferably flat and large to maximize the light collected and transmitted to the needle end 4 of the probe 1.

Figure 2:
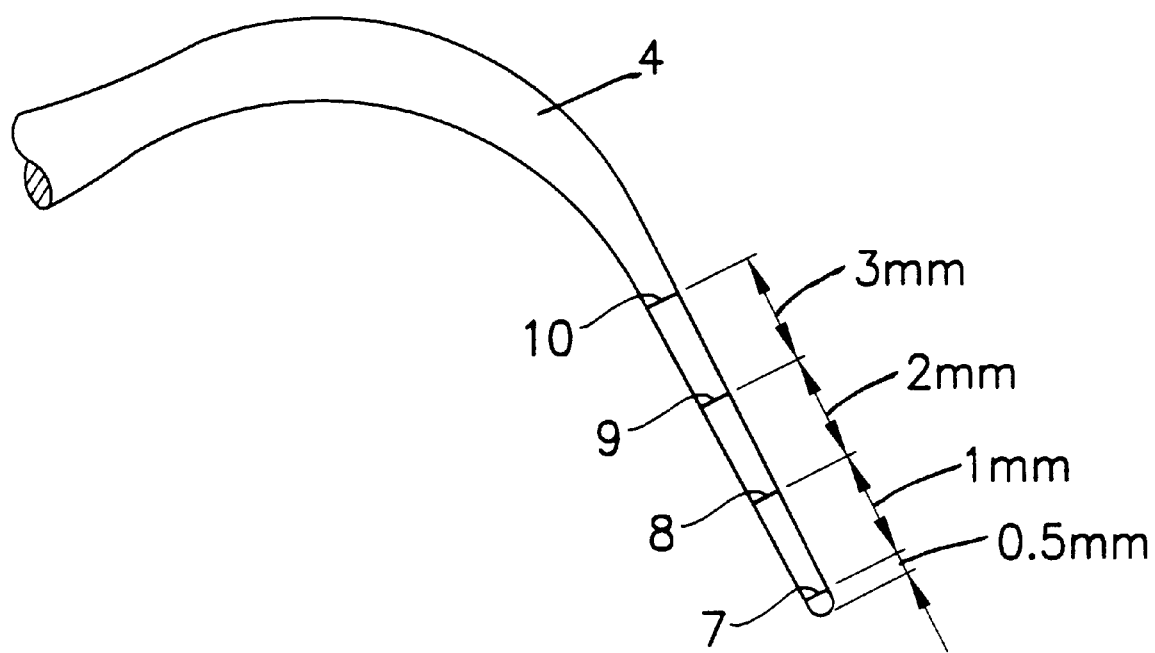
FIG. 2 is an enlarged view of an embodiment of the measuring needle of the dental probe.
Figure 3:
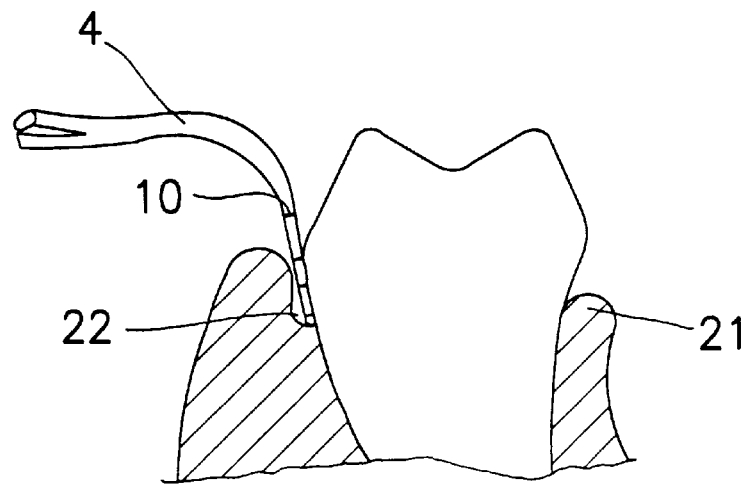
FIG. 3 shows the measurement of the depth of a gum pocket using an embodiment of the dental probe.
Figure 4:
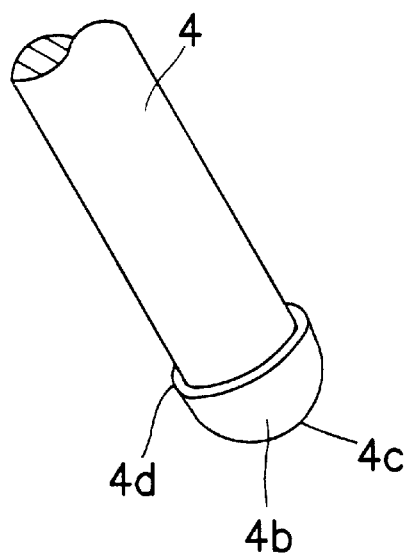
FIG. 4 is an enlarged view of an embodiment of the measuring needle showing a hemispherical tip.

The measuring needle 4 may have etched measurement gradations such as 0.5 7, 1 mm 8, 2 mm 9, and 3 mm 10 s shown in FIG. 2. The position of the gradations can be freely adapted and depends on the desired units and precision of measurement. As shown in FIG. 3, the user can easily obtain an accurate measurement of the pocket's 22 depth even in a dark mouth cavity by viewing one of the indicators 10 on the measuring needle 4 illuminated by the light reflected through the probe to the needle edge.

Figure 5:
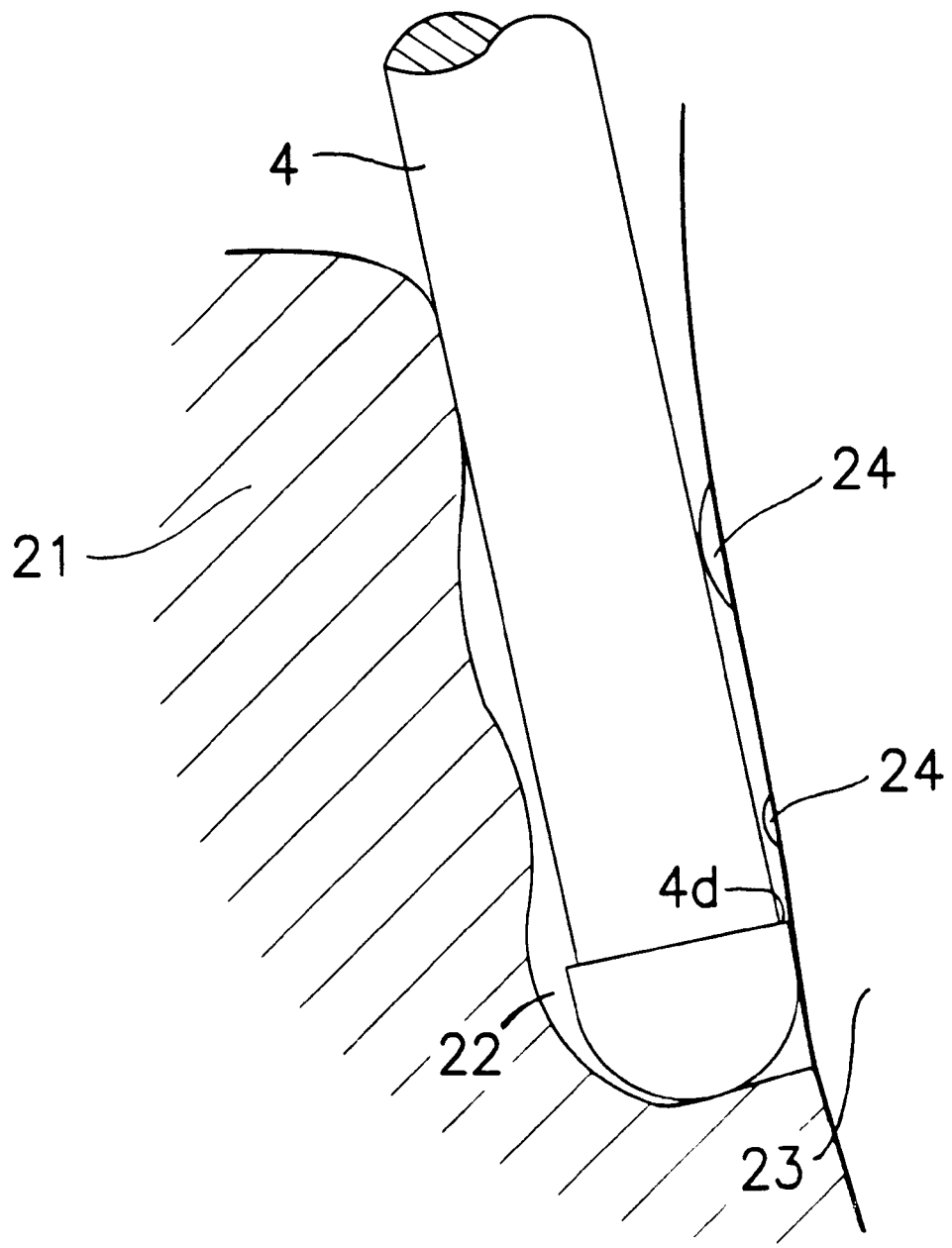
FIG. 5 is an enlarged view of an embodiment of the measuring probe being used to probe the existence and the position of tartar and foreign matters.

The measuring needle tip 4b may have a hemispherical form and is connected to the measuring needle, the diameter of which may be a little smaller than the diameter of the hemisphere 4c at the junction of the needle 4 and the hemisphere 4c, so that an annular ledge 4d for probing the location of tartar is formed at the junction. As shown in the FIG. 5, the hemispherical tip of the measuring needle can measure the pocket's 22 depth and probe the pocket 22 itself. After measuring the pocket's 22 depth, dentists can probe the existence and the position of tartar 24 and other foreign matters by gradually pulling out the measuring needle from the blind pocket 22, and by feeling for a rugged surface on the root 23 of the tooth as the annular ledge 4d formed by the junction of the needle and the hemisphere brushes against the root 23 of the tooth. Also, the hemispherical form of the needle tip will not easily wound the patient's gum 21.

The probe is manufactured from transparent lighting plastic preferably containing a fluorescent dye. Examples of such transparent plastic are acryl, polystyrene or polycarbonate, which can be combined with a special fluorescent dye like Morgen-F of BASF. STEEL-LIGHT of Fujitsu-Kasei Co., Ltd., and LISA-PALASTIC of BAYER are commercial examples of the combined transparent lighting fluorescent plastic.

Figure 6:
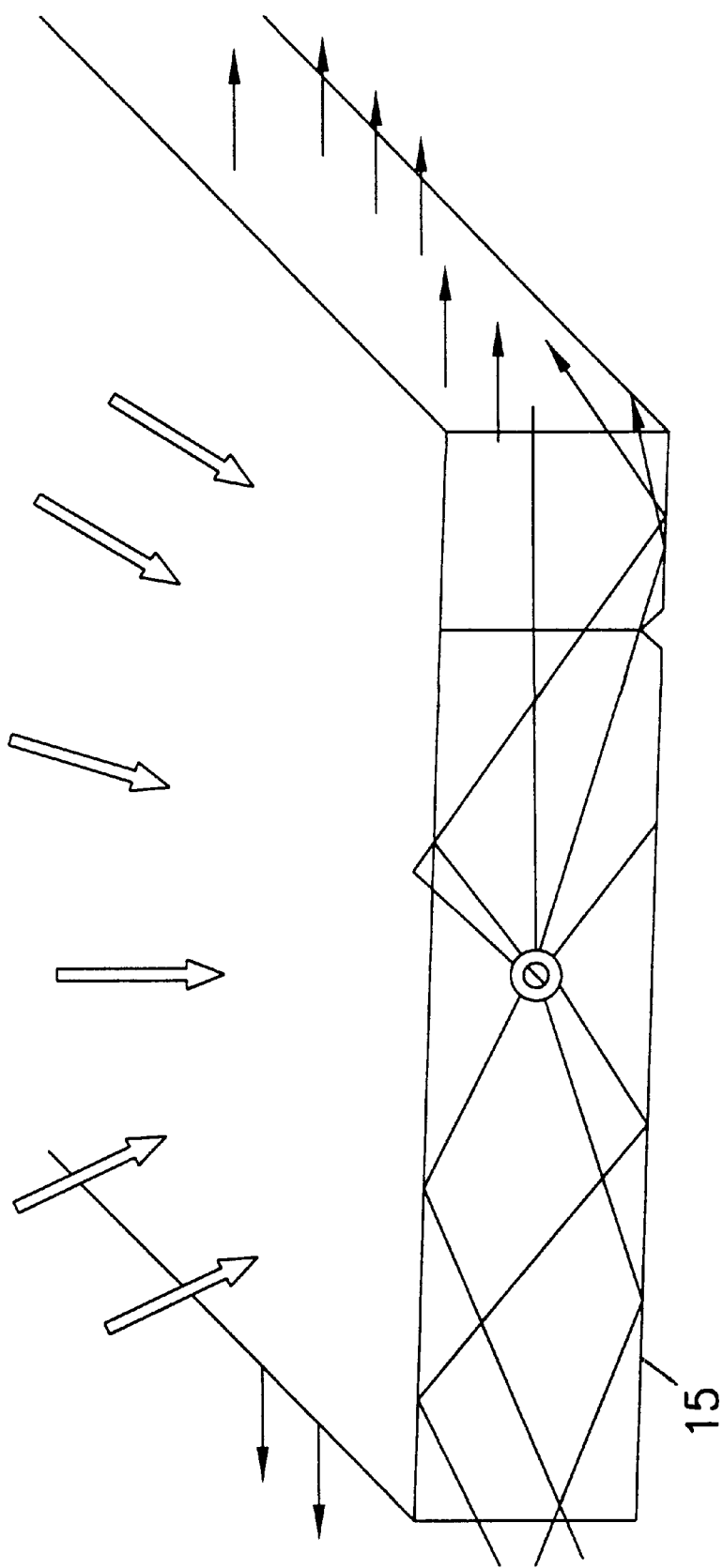
FIG. 6 shows the transmission of light in light condensing fluorescent plastic.

The light condensing properties of the fluorescent plastic are shown in FIG. 6. Almost ninety percent of the collected light will be conducted through the plastic 15 and will be radiated to the edge of the needle. Thus, the gradations on the edge of the measuring probe are effectively illuminated by direct and/or dispersed light collected from the distal end of the probe.

The plastic probe is light and highly maneuverable in the mouth cavity. The probe is also made as one piece by injection molding, so the production cost of the probe is very low. It is also disposable, a feature which completely eliminates the danger of transmitting a contagious disease or blood to another patient. Thus an inexpensive, easily-handled, disposable and luminous probe can be provided to dentists. Additionally, unlike a traditional measuring probe using a stainless needle, this probe made of fluorescent plastic can be inserted in a space between the patient's gum and tooth without wounding the gum. And the hemispherical ledge on the measuring portion of the probe can probe the existence and the position of the tartar and foreign matters at the same time as it measures the pocket's depth. This is helpful for early treatment of Riggs' disease. All of these features and the probe's ability to operate in low lighting conditions make the probe ideal for use in an industrial setting.

What is claimed is:

1. A one-piece dental probe for measuring and exploring the depth of a blind pocket formed around a tooth, said probe made of transparent light condensing fluorescent plastic, said probe comprising:

a) an elongated handle having a first end and a second end;

b) a distal portion at said second end of said handle for collecting light, said distal portion is a substantially flat surface so as to maximize the light collected and reflected into said probe; and c) a measurement needle at said first end of said handle for probing the blind pocket and for dispersing light collected from said distal portion to illuminate a vicinity of the blind pocket, said measurement needle further comprising at least one measurement gradation for measuring the depth of the blind pocket.

2. The dental probe of claim 1, wherein the area of said substantially flat surface is large relative to that of a cross-section of said handle so as to further maximize the light collected and reflected into said probe.

3. The dental probe of claim 1, wherein said needle has a hemispherical tip.

4. The dental probe of claim 3, wherein the diameter of said needle is smaller than the diameter of the needle tip at the junction of the needle and the needle tip such that an annular ledge is formed at the junction of the needle and the needle tip.

5. The dental probe of claim 1, wherein said measurement needle has a first curve and a second curve, said first curve being closer to said handle than said second curve, said second curve disposed at approximately a 60 degree angle relative to said handle.

* * * * *